United States Patent [19]

McKee et al.

[11] 3,950,375

[45] Apr. 13, 1976

[54] CONTINUOUS MANUFACTURE OF PEROXYDICARBONATES

[75] Inventors: Peter M. McKee; Uday D. Wagle, both of Grand Island, N.Y.

[73] Assignee: Pennwalt Corporation, Philadelphia, Pa.

[22] Filed: Dec. 10, 1973

[21] Appl. No.: 423,350

[52] U.S. Cl. ............................................. 260/463
[51] Int. Cl.² ...................................... C07C 179/18
[58] Field of Search .................................. 260/463

[56] References Cited
UNITED STATES PATENTS

| | | | |
|---|---|---|---|
| 3,377,373 | 4/1968 | Lederer et al. | 260/463 |
| 3,429,910 | 2/1969 | Lederer et al. | 260/463 |

OTHER PUBLICATIONS

The Condensed Chemical Dictionary, 6th Ed., Reinhold Publishing Corp., N.Y., pp. 629–630 (1961).
Strain et al., J. Am. Chem. Soc., Vol. 72, pp. 1254–1255 (1950).

*Primary Examiner*—Richard J. Gallagher
*Assistant Examiner*—Diana G. Rivers
*Attorney, Agent, or Firm*—David Edwards

[57] ABSTRACT

A continuous solvent-free process for the manufacture of peroxydicarbonates from chloroformate, hydrogen peroxide and alkali metal hydroxide utilizing at least two reactors and a centrifuge to separate high purity product.

15 Claims, 1 Drawing Figure

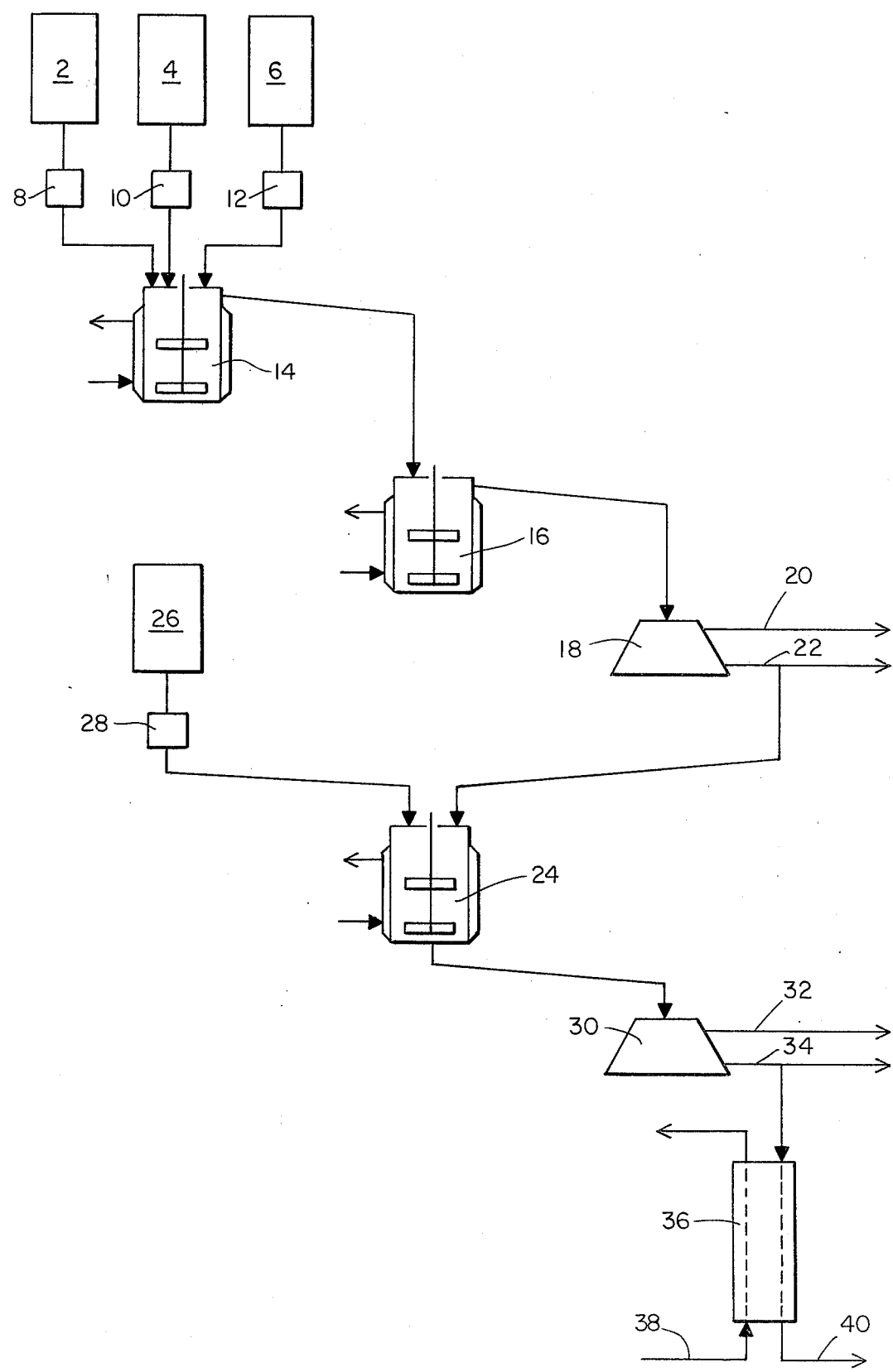

CONTINUOUS MANUFACTURE OF PEROXYDICARBONATES

BACKGROUND OF THE INVENTION

The present invention relates to a process and apparatus for the continuous manufacture of peroxydicarbonates in high purity.

Peroxydicarbonates, RO-C(O)-OO-C(O)-OR, have recently gained considerable importance as initiators in the polymerization field since they can be used in substantially reduced amounts in comparison to peroxyester initiators, R-C(O)-OO-R. One of the disadvantages of peroxydicarbonates, however, especially in their process of manufacture, is their inherent stability. Peroxydicarbonates such as diisopropylperoxydicarbonate (IPP) and di-n-propylperoxydicarbonate (NPP) are very sensitive both thermally and to heavy shock. Both are capable of detonating under certain conditions. For example, on standing at room temperature IPP decomposes with vigorous gassing and the vapors may autoignite.

The preparation of peroxydicarbonates must therefore be carried out with precautionary measures provided to prevent decomposition from either heat or impact. In commercial batch processes where large amounts are handled in order to be economical, serious explosions have occurred in making pure product. The other alternative has been to use diluents or inert solvents in the process and to sell a dilute product.

For example, U.S. Pat. No. 3,377,373 describes a process for the continuous manufacture of peroxydicarbonates wherein a chloroformate (or chlorocarbonic acid ester) is reacted with hydrogen peroxide and an aqueous alkali metal hydroxide solution in at least two reaction zones, the reaction being terminated in the last or after-reaction zone by addition of a halogenated organic solvent or a liquid halogen-free hydrocarbon solvent. The solvent solution is then isolated by using various settling vessels, washing vessels and the like. A similar continuous process using solvents is described in U.S. Pat. No. 3,429,910.

Since the use of solvents decreases the efficiency of processing and since pure (undiluted) peroxydicarbonates are desired for many polymerization processes, it would be highly desirable to have a continuous, solvent-free process which would increase processing efficiency and be capable of providing the polymerization industry with a choice of either pure or diluted products.

Brief Summary of the Invention

The present invention relates to an improved, solvent-free, process for the continuous manufacture of peroxydicarbonates of the formula RO-C(O)-OO-C(O)-OR, wherein R is alkyl of 2–16 carbons, by continuously reacting chloroformate of the formula RO-C(O)-Cl with hydrogen peroxide and aqueous alkali metal hydroxide at a temperature in the range of about −10° to +50°C. in at least two reaction zones connected in series, the improvement residing in continuously feeding the (undiluted) reaction mixture from the last of said reaction zones through a centrifuge to isolate peroxydicarbonate product (the organic phase) in at least about 97% purity (assay). Optionally, the purity can be further improved to at least about 98% by continuously mixing the isolated organic phase from the centrifuge with a saturated salt solution in a mixing zone and continuously feeding the organic phase-salt solution mixture through a second centrifuge to again recover the organic phase. Still further increase in purity (to at least about 99%) as well as reduction in water, chloroformate and chloride content can be obtained by continuously passing the recovered organic phase from the second centrifuge through a stripping zone where the product is subjected to stripping with dry air or other oxygen-containing gas in a stripping column.

Detailed Description of the Invention

It has now been discovered that peroxydicarbonates can be continuously produced safely and in high purity in an efficient, solvent-free process by employing centrifuges to isolate pure product. The basic process to which this improvement relates is substantially described in U.S. Pat. No. 3,377,373 which description is incorporated herein by reference.

More specifically, it has been found that peroxydicarbonates of the formula RO-C(O)-OO-C(O)-OR can be advantageously prepared in high purity (at least about 97% assay) by the improved continuous process, each R being separately selected from alkyl of 2 to 16 carbons (preferably 3–8) including linear or branched alkyl, cycloalkyl, and substituted or unsubstituted alkyl such as ethyl, isopropyl, butyl, 2-ethylhexyl, benzyl, cyclohexyl, 2-phenoxyethyl, tetradecyl, cetyl and the like. The reaction of a chloroformate, RO-C(O)-Cl, where R is as above defined, with aqueous hydrogen peroxide and aqueous alkali metal hydroxide is carried out at a temperature in the range of from about −10°C. to about +50°C. (preferably about 10°–35°C.) in apparatus including at least two jacketed reactors (14 and 16) and a centrifuge (18) connected in series. While two series connected reactors are generally sufficient, more may be desired to increase the residence time in the reaction zone when dealing with the less reactive chloroformates (such as where R has 13–16 carbons).

The reactants are continuously added from storage tanks 2, 4 and 6) at controlled flow rates via metering devices (8, 10 and 12) to reactor 14 where a major portion (normally 90–95%) of the reaction takes place, the temperature of the reaction mixture being maintained with ± 1°C. of that desired (normally about 20°–35°C. in reactor 14). The reaction mixture then flows to the second reactor (16) where the remainder of the reaction occurs and where the temperature is preferably lowered to about 9°–11°C. since slight heating occurs during centrifugation. Both reactors are provided with efficient agitation and cooling means such as described in U.S. Pat. No. 3,377,373.

The cooled reaction mixture is then continuously fed through a centrifuge to isolate the peroxydicarbonate product. A few of the peroxydicarbonate products are solids (for example, where R is cyclohexyl, tetradecyl, cetyl) and are recovered with liquid-solid centrifuges, but most are liquids and are recovered in liquid-liquid centrifuges, the organic phase containing the peroxydicarbonate product being separated from the aqueous phase. Conventional centrifuges of either the basket, bowl or disc type can be employed, disc type centrifuges being used in the examples to follow. The aqueous phase (stream 20) is discarded and the product (22, of at least about 97% purity) can be packed out directly from the centrifuge or processed further by continuously mixing the product in mixing tank 24 with a saturated salt solution which is added at a controlled flow rate through metering device 28 from storage tank 26. The temperature in mixing tank 24 (provided with agitation and cooling means as in reactors 14 and 16) is again preferably maintained near the lower part of the range, normally about 10°C. The mixed solution is then continuously fed through a second centrifuge (30) of the above-described type to isolate a product (stream 34) of at least about 98% purity, the aqueous phase (stream 32) again being discarded.

If still further increase in purity (to at least about 99% assay) and reduction in alkyl chlorides, chloroformate and water content is desired, the product stream (34) from centrifuge 30 is continuously fed through a stripping zone (normally a stripping column 36 containing packing or plates) where it is subjected to stripping (normally countercurrent or cross-flow) with dry air or other oxygen containing gas (38) at ambient temperatures. The column preferably will have at least two theoretical plates. The product (40) can either be packed out as is (pure) or diluted with various solvents (e.g., toluene, acetone, methylcyclohexane, odorless mineral spirits).

The storage tanks (2, 4, 6, 26) and controls (8, 10, 12, 28) can be constructed of any type material compatible with the reactant to be stored or pumped. The mix tank (24) can be of glass or stainless steel. Reactors (14 and 16) are preferably made of stainless steel, reactor 14 also being equipped with a pH meter to monitor pH of the reaction in the 8–14 range (preferably 10–12).

The chloroformate starting material should have a minumum assay (purity) of at least about 90% (preferably at least 97–98%). With purer starting materials, the second centrifuge and stripper can often be avoided. 30–70% Aqueous hydrogen peroxide (preferably 50%) and 10–50% aqueous alkali metal hydroxide (preferably 20% sodium or potassium hydroxide) solutions are advantageously used as the other starting components. The reactants are mixed in a ratio of 0.9–1.1 (preferably 1.0) mole of hydrogen peroxide to 2.0–2.2 (preferably 2.0) moles of chloroformate to 1.9–2.4 (preferably 2.0) moles of aqueous hydroxide. The saturated salt solution can be various water soluble inorganic salts such as ammonium, sodium and potassium chlorides, sulfates and phosphates (sodium chloride being preferred), the amount of solution normally being about equal to the amount of product from the first centrifuge. While the above description defines process and apparatus for preparing symmetrical peroxydicarbonates (where the R groups are the same), mixed percarbonates can be prepared by introducing two chloroformates (with different R groups) into reactor 14, the remainder of the process being the same.

The following examples illustrate the invention but are not in limitation thereof. Flow rates are in parts by weight/hour (pph) unless otherwise indicated. The reactors (14 and 16) are of stainless steel and mix tank 24 is glass. the centrifuges (18 and 30) are liquid-liquid centrifuges of the desludging disk type.

EXAMPLE I

Continuous preparation of Di-sec-butylperoxydicarbonate (SBP)

The rate of flow of reactants to obtain a yield of 30 pph of product is: 50 pph of di-sec-butyl chloroformate, 19.5 pph of 50% aqueous $H_2O_2$, and 99 pph of 20% aqueous NaOH. The temperature of reactor 14 is maintained at 35 ± 1°C., and that of reactor 16 at 10 ± 1°C. by circulating cooling brine through the cooling jackets of the reactors. Product stream 22 from centrifuge 18 has an average assay of 97.5%. When product stream 22 is mixed in wash tank 24 with 30 pph of saturated sodium chloride solution and run through centrifuge 30, product stream 34 has an average assay of greater than 98%.

EXAMPLE II

Preparation of Di-n-propylperoxydicarbonate (NPP)

Using the apparatus (i.e., both centrifuges 18 and 30) and procedure of Example I (except that the temperature of reactor 14 is 25 ± 1°C.), NPP is prepared at the rate of 50 pph in an average assay of greater than 98% from 85 pph of n-propyl chloroformate, 31 pph of 50% aqueous $H_2O_2$, 169 pph of 20% NaOH and 50 pph of saturated NaCl solution.

EXAMPLE III

Preparation of Diisopropylperoxydicarbonate (IPP)

Following the Example II procedure, IPP is prepared at the rate of 50 pph in an average assay of greater than 98% from 85 pph of isopropyl chloroformate, 28.5 pph of 50% $H_2O_2$, 160 pph of 20% NaOH and 50 pph of saturated NaCl solution.

EXAMPLES IV TO IX

Following the processes of Examples I and III, additional runs of IPP and SBP are illustrated below in Table I to show the effect of stripping product stream 34 with dry air at room temperature through packed column 36 on the assay and chlorides content:

TABLE I

| Example | Product | FLOW RATES (pph) | | | | | Reactor Temp.(°C.) | | Stream 34 | | Stream 40 | |
|---|---|---|---|---|---|---|---|---|---|---|---|---|
| | | 50% $H_2O_2$ | 20% NaOH | Chloroformate | NaCl | Product | No. 14 | No. 16 | % Assay | % Cl | % Assay | % Cl |
| IV | IPP | 28 | 168 | 72 | 50 | 50 | 25 | 11 | — | — | 100 | 0.03 |
| V | IPP | 28 | 165 | 73 | 50 | 50 | 25 | 10 | 98.5 | 0.32 | 99.4 | 0.11 |
| VI | IPP | 27 | 157 | 84 | 50 | 50 | 25 | 10 | 98.9 | 0.30 | 99.1 | 0.24 |
| VII | SBP | 19 | 99 | 48 | 30 | 30 | 30 | 11 | — | — | 99.7 | 0.07 |
| VIII | SBP | 19 | 94 | 50 | 30 | 30 | 30 | 10 | — | — | 99.7 | 0.06 |
| IX | SBP | 18 | 95 | 50 | 30 | 30 | 30 | 9 | 98.2 | — | 99.4 | 0.16 |

What is claimed is:

1. In a process for the continuous manufacture of peroxydicarbonate, RO-C(O)-OO-C(O)-OR wherein R is alkyl of 2–16 carbons, by continuously reacting chloroformate, RO-C(O)-Cl, with hydrogen peroxide and aqueous alkali metal hydroxide at a temperature in the range of −10°C. to +50°C. in at least two reaction zones connected in series, the improvement which comprises isolating peroxydicarbonate product in at least 97% purity by continuously feeding a solvent-free reaction mixture from the last of said reaction zones directly through a centrifuge to recover the organic phase.

2. The process of claim 1 wherein R is alkyl of 3–8 carbons and said centrifuge is a liquid-liquid centrifuge.

3. The process of claim 2 wherein R is isopropyl.

4. The process of claim 2 wherein R is secondary butyl.

5. The process of claim 2 wherein R is n-propyl.

6. The process of claim 1 which further comprises continuously mixing the isolated organic phase with saturated salt solution in a mixing zone and isolating peroxydicarbonate product of at least 98% purity by continuously feeding the mixed organic phase-salt solution through a second centrifuge to recover the organic phase.

7. The process of claim 6 wherein R is alkyl of 3–8 carbons and both centrifuges are liquid-liquid centrifuges.

8. The process of claim 7 wherein R is isopropyl.

9. The process of claim 7 wherein R is secondary butyl.

10. The process of claim 7 wherein R is n-propyl.

11. The process of claim 6 which further comprises continuously passing the organic phase recovered from the second centrifuge through a stripping zone where the organic phase is subjected to stripping with dry oxygen-containing gas in a column and recovering peroxydicarbonate product of at least 99% purity.

12. The process of claim 11 wherein R is alkyl of 3–8 carbons and both centrifuges are liquid-liquid centrifuges.

13. The process of claim 12 wherein R is isopropyl.

14. The process of claim 12 wherein R is secondary butyl.

15. The process of claim 12 wherein R is n-propyl.

* * * * *